US00PP11841P2

(12) United States Plant Patent

Zary

(10) Patent No.: US PP11,841 P2
(45) Date of Patent: Apr. 24, 2001

(54) FLORIBUNDA ROSE PLANT NAMED 'JACTASY'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/266,993

(22) Filed: Mar. 12, 1999

(51) Int. Cl.[7] ..... A01H 5/00
(52) U.S. Cl. ..... Plt./144
(58) Field of Search ..... Plt./144, 133

*Primary Examiner*—Howard J. Locker
(74) *Attorney, Agent, or Firm*—Klarquist Sparkman Campbell Leigh & Whinston, LLP

(57) ABSTRACT

Floribunda rose plant having a strong upright growth, long stems, excellent clustering ability, resistance to powdery mildew and long vase life.

1 Drawing Sheet

The present invention relates to a new and distinct variety of rose plant of the floribunda class which was originated by me by crossing the variety 'INTERprince', U.S. Plant Pat. No. 8,102, with an unnamed seeding (unnamed seedling× unnamed seedling).

The primary objective of this breeding was to produce a new rose variety combining the strong, upright growth, long stems, and the ability to flower in clusters of the female parent combined with the clustering ability, resistance to powdery mildew and long vase life of the male parent. The objective was substantially achieved, along with other desirable improvements, as evidenced by the following unique combination of characteristics that are outstanding in the new variety and that distinguish it from its parents, as well as from all other varieties of which I am aware:

1. Excellent clustering ability;
2. Long stems;
3. Strong, upright growth;
4. Resistance to powdery mildew;
5. Good vase life.

'JACtasy' is a greenhouse cut rose variety. It blooms in clusters of four to seven flowers on stems averaging 18–22" in length and yielding 160–180 flowers/$m^2$ of greenhouse.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent*.—'INTERprince', U.S. Plant Pat. No. 8,102.

*Pollen parent*.—Unnamed seedling (unnamed seedling×unnamed seedling)

Classification:

*Botanical*.—*Rosa hybrida*.

*Commercial*.—Floribunda.

FLOWER

Observations made from specimens grown in a garden environment at Somis, Calif., February 1997 to December 1998.

Blooming habit: Continuous.

Bud:

*Size*.—One and one-half inches long when the petals start to unfurl.

*Form*.—The bud form is long, pointed ovoid.

*Color*.—When sepals first divide, bud color is White Group 155B on the outer three-quarters of the petals. The inner one-quarter of the petals is close to Yellow Group 11D. When half blown, the upper sides of the petals are White Group 155B on the outer three-quarters of the petals. The inner one-quarter of the petals is close to Yellow Group 11D. The lower sides of the petals are White Group 155B except near the base of the petal where they are close to Yellow Group 11D.

*Sepals*.—Color: Green Group 138B. Surface texture: Covered in fine hairs. There are three lightly appendaged sepals. There are two unappendaged sepals with hairy edges.

*Receptacle*.—Color: Yellow-Green Group 146B. Shape: Funnel. Size: Small, about 5/16"×1/4". Surface: Smooth.

*Peduncle*.—Length: Short, averaging about two inches. Surface: Glandular. Color: Yellow-Green Group 146B. Strength: Stiff, erect.

Bloom:

*Size*.—Medium. Average open size is about three and one-half inches.

*Borne*.—Several together in somewhat flat to pyramidal clusters of four to seven blooms.

*Stems*.—Strength: Strong. Average length is about eighteen to twenty-two inches.

*Form*.—When first open: High-centered. Permanence:. Flattens, all petals curl with some quilling.

*Petalage*.—Number of petals under normal conditions: 25–30.

*Color*.—The upper sides of the petals are White Group 155B with the inner one-quarter of the petals close to Yellow Group 11D. The reverse sides of the petals are White Group 155D with a small area near the base of the petals Yellow Group 11D. The base of each petal has on the upper surface a ⅛"×⅛", Yellow Group 11A color spot. On the lower surface there is a smaller spot, 1/16"×1/16", Yellow Group 11A color spot. The major color on the upper sides is White Group 155B.

*Variegations*.—There are occasional green streaks on both surfaces of the guard petals. The color is close to Yellow-Green Group 146B.

*Discoloration*.—The general tonality at the end of the first day: No change. At the end of the third day: No change. By day ten in the vase, all yellow has left the petals except for the color spot. Petal drop is by day twelve.

*Fragrance*.—None.

Petals:

*Texture*.—Thick.

*Shape*.—Oval to slightly deltoid.

*Form*.—Tips slightly recurved, edges slightly quilled.

*Arrangement*.—Imbricated. Petaloids in the center: None.

*Persistence*.—Petals drops off cleanly before drying.

*Lastingness*.—On the plant: Long (twelve days). As a cut flower: Long (about twelve days).

Reproductive parts:

*Anthers*.—Size: Medium. Quantity: Many. Color: Yellow-Orange Group 22C. Arrangement: Regular around styles.

*Filaments*.—Color: Yellow Group 13B.

*Pollen*.—Present.

*Styles*.—Color: Green-White Group 157D.

*Stigmas*.—Color: Yellow-White Group 158C.

Plant:

*Form*.—Bush.

*Growth*.—Vigorous, upright, branching. Mature plant height is about five and one-half feet, width is about three and one-half feet.

Foliage: Number of leaflets on normal mid-stem leaves: Five or sometimes seven.

*Size*.—Large (about 6" long×4½" wide).

*Quantity*.—Abundant.

*Color*.—New foliage: Upper and lower surfaces: Greyed-Orange Group 176A. Old foliage: Upper surface: Green Group 137B. Lower surface: Green Group 137D.

Leaflets:

*Shape*.—Pointed oval.

*Texture*.—Leathery.

*Edge*.—Serrated.

*Serration*.—Single, small.

*Petiole rachis*.—Color: Green Group 137C.

*Petiole underside*.—Rough with prickles and glands.

*Stipules*.—Medium (½"), serrated, bearded.

*Disease resistance*.—Resistant to mildew and rust under normal growing conditions in a greenhouse. Not tested for blackspot.

Wood:

*New wood*.—Color: Green Group 137C. Bark: Smooth.

*Old wood*.—Color: Green Group 137A. Bark: Smooth.

Prickles:

*Quantity*.—On main canes from base: Ordinary. On laterals from main canes: Ordinary.

*Form*.—Medium, hooked slightly downward.

*Color when young*.—Greyed-Purple Group 183C.

*Color when mature*.—Greyed-Orange Group 166A.

Small prickles:

*Quantity*.—On main stalks: None. On laterals: None.

I claim:

1. A new and distinct variety of rose plant of the floribunda class, substantially as herein shown and described, characterized particularly by its strong upright growth, long stems, excellent clustering ability, resistance to powdery mildew and long vase life.

* * * * *

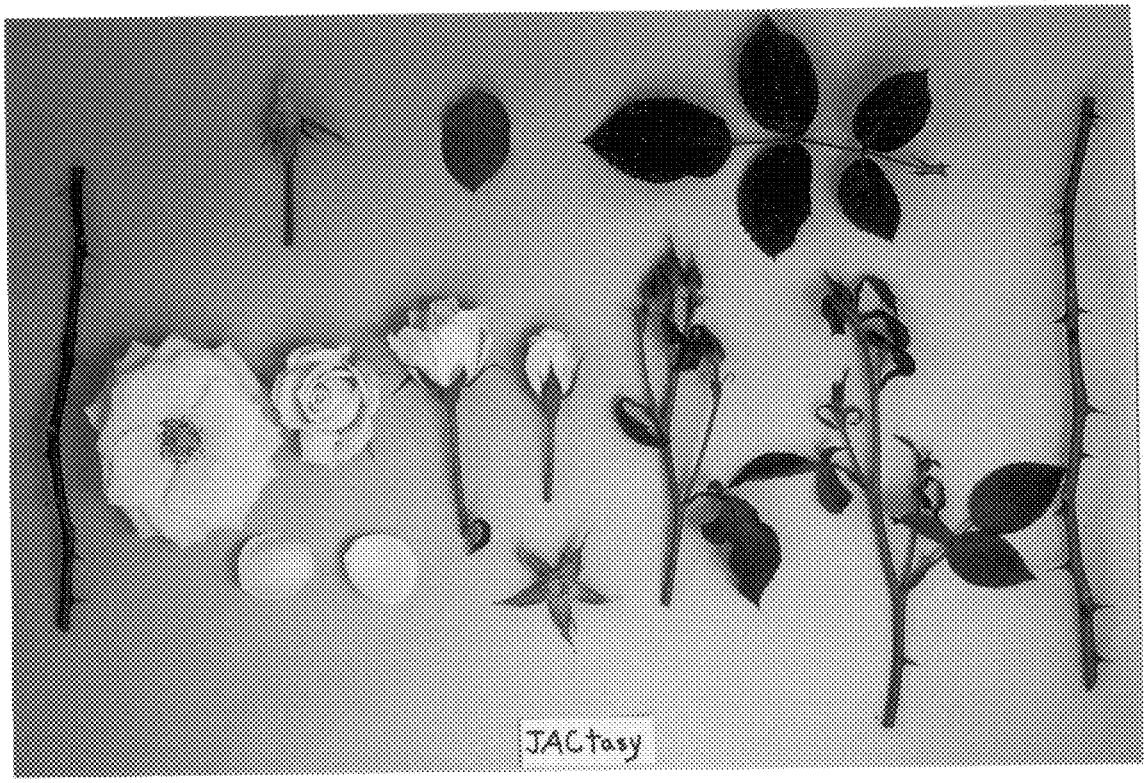
JACtasy